(12) United States Patent
Nara et al.

(10) Patent No.: US 11,698,428 B2
(45) Date of Patent: Jul. 11, 2023

(54) INFORMATION PROCESSING APPARATUS AND INFORMATION PROCESSING METHOD

(71) Applicants: The University of Tokyo, Tokyo (JP); CANON MEDICAL SYSTEMS CORPORATION, Tochigi (JP)

(72) Inventors: Takaaki Nara, Bunkyo-ku (JP); Motofumi Fushimi, Bunkyo-ku (JP); Naohiro Eda, Bunkyo-ku (JP); Seiichi Shin, Moriya (JP); Hitoshi Yamagata, Otawara (JP); Koji Yano, Otawara (JP); Hiroyuki Fujita, Toshima (JP)

(73) Assignees: The University of Tokyo, Tokyo (JP); CANON MEDICAL SYSTEMS CORPORATION, Tochigi (JP)

( * ) Notice: Subject to any disclaimer, the term of this patent is extended or adjusted under 35 U.S.C. 154(b) by 0 days.

(21) Appl. No.: 17/585,742

(22) Filed: Jan. 27, 2022

(65) Prior Publication Data
US 2022/0236352 A1 Jul. 28, 2022

(30) Foreign Application Priority Data

Jan. 27, 2021 (JP) .................................. 2021-011545
Jan. 25, 2022 (JP) .................................. 2022-009328

(51) Int. Cl.
*G01R 33/44* (2006.01)
*G01R 33/563* (2006.01)
(Continued)

(52) U.S. Cl.
CPC .......... *G01R 33/443* (2013.01); *A61B 5/0042* (2013.01); *A61B 5/055* (2013.01);
(Continued)

(58) Field of Classification Search
CPC . A61B 5/0042; A61B 5/055; A61B 2576/026; G01R 33/5608; G01R 33/56358
See application file for complete search history.

(56) References Cited

U.S. PATENT DOCUMENTS

| 5,592,085 A | 1/1997 | Ehman |
| 2012/0271571 A1* | 10/2012 | Bulumulla ........... G01R 33/246 |
| | | 702/57 |

(Continued)

FOREIGN PATENT DOCUMENTS

WO 2013/057655 A1 4/2013

OTHER PUBLICATIONS

Katscher, U., et al., "Electric Properties Tomography: Biochemical, Physical and Technical Background, Evaluation and Clinical Applications", NMR in Biomed., vol. 30, Mar. 14, 2017, e3729, pp. 1-15.

(Continued)

*Primary Examiner* — Gregory H Curran
(74) *Attorney, Agent, or Firm* — Oblon, McClelland, Maier & Neustadt, L.L.P.

(57) ABSTRACT

An information processing apparatus according to an embodiment includes a processing circuit. The processing circuit acquires a measurement field corresponding to a spatial distribution of a predetermined physical quantity in a subject of measurement. The processing circuit calculates an unknown quantity in the subject of measurement based on a first equation between the measurement field and the unknown quantity having spatial dependence, and on the acquired measurement field. The first equation is one that is acquired based on a second equation expressing a dual field divergence of which can be expressed using the measurement field, by using the measurement field and the unknown quantity, and on the Helmholtz decomposition of the dual field.

15 Claims, 8 Drawing Sheets

(51) Int. Cl.
*G01R 33/56* (2006.01)
*A61B 5/00* (2006.01)
*A61B 5/055* (2006.01)
*G01R 33/48* (2006.01)

(52) U.S. Cl.
CPC ..... *G01R 33/4806* (2013.01); *G01R 33/5608* (2013.01); *G01R 33/56358* (2013.01); *A61B 2576/026* (2013.01)

(56) References Cited

U.S. PATENT DOCUMENTS

2014/0300354 A1* 10/2014 He ................... G01R 33/246
324/309
2014/0316245 A1* 10/2014 Romano ............ A61B 5/4064
600/410

OTHER PUBLICATIONS

Liu, J., et al., "Electrical Properties Tomography Based on $B_1$ Maps in MRI: Principles, Applications, and Challenges", IEEE Trans. Biomed. Eng., vol. 64, No. 11, Nov. 2017, pp. 2515-2530.
Chi, J., et al., "Magnetic Resonance-Electrical Properties Tomography by Directly Solving Maxwell's Curl Equations", Appl. Sci., vol. 10, No. 9, May 10, 2020, 3318, pp. 1-13.

* cited by examiner

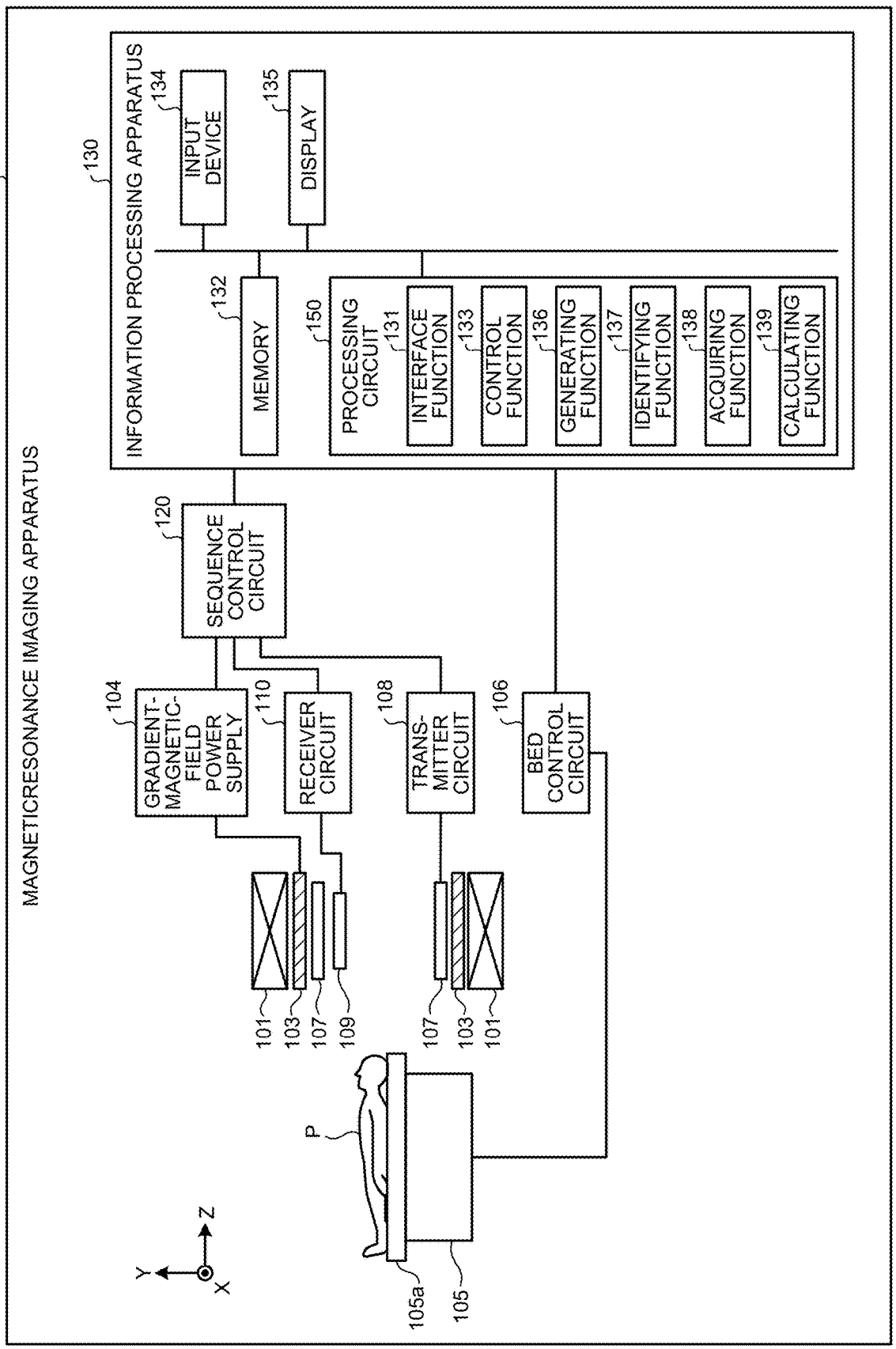

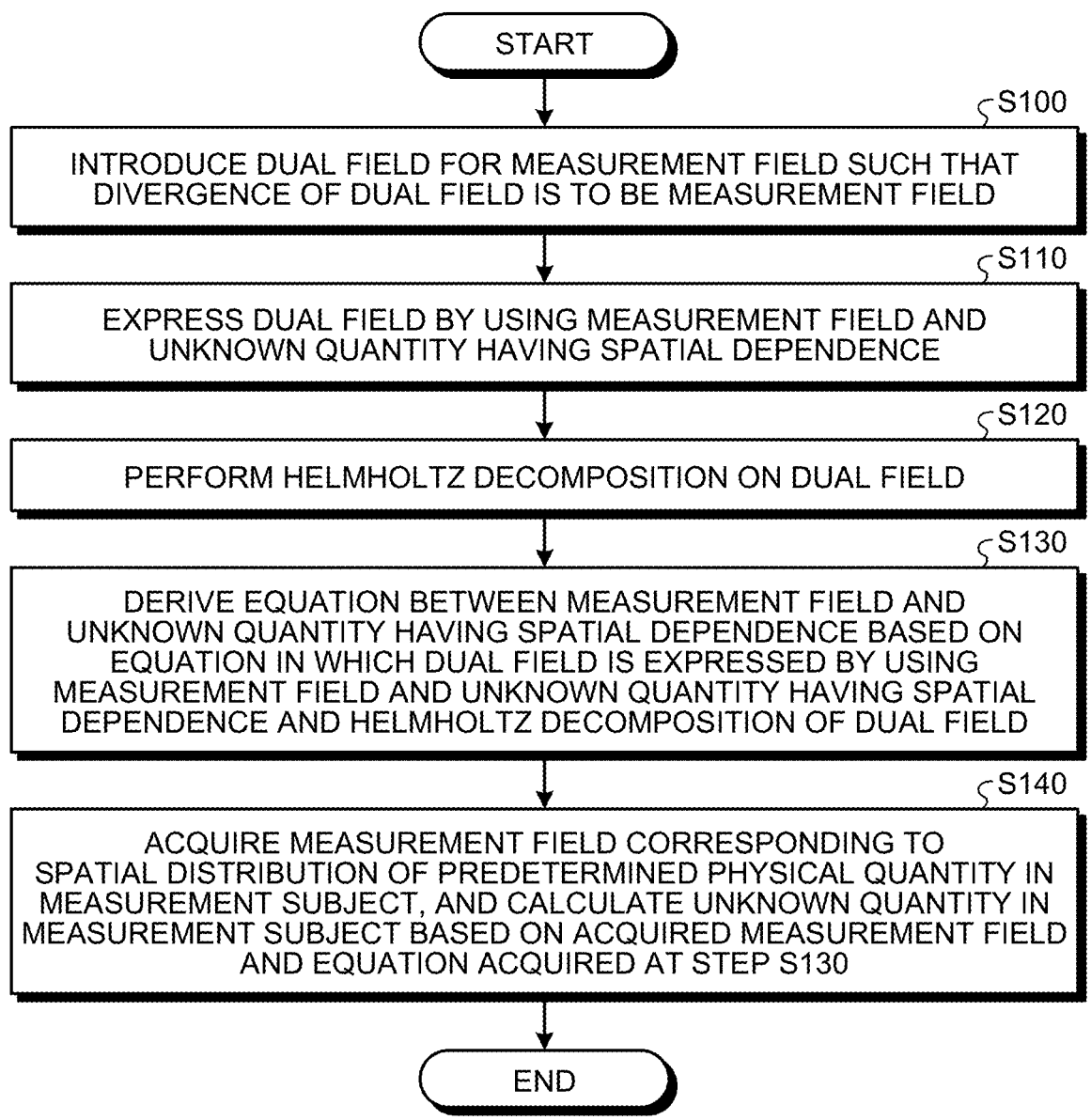

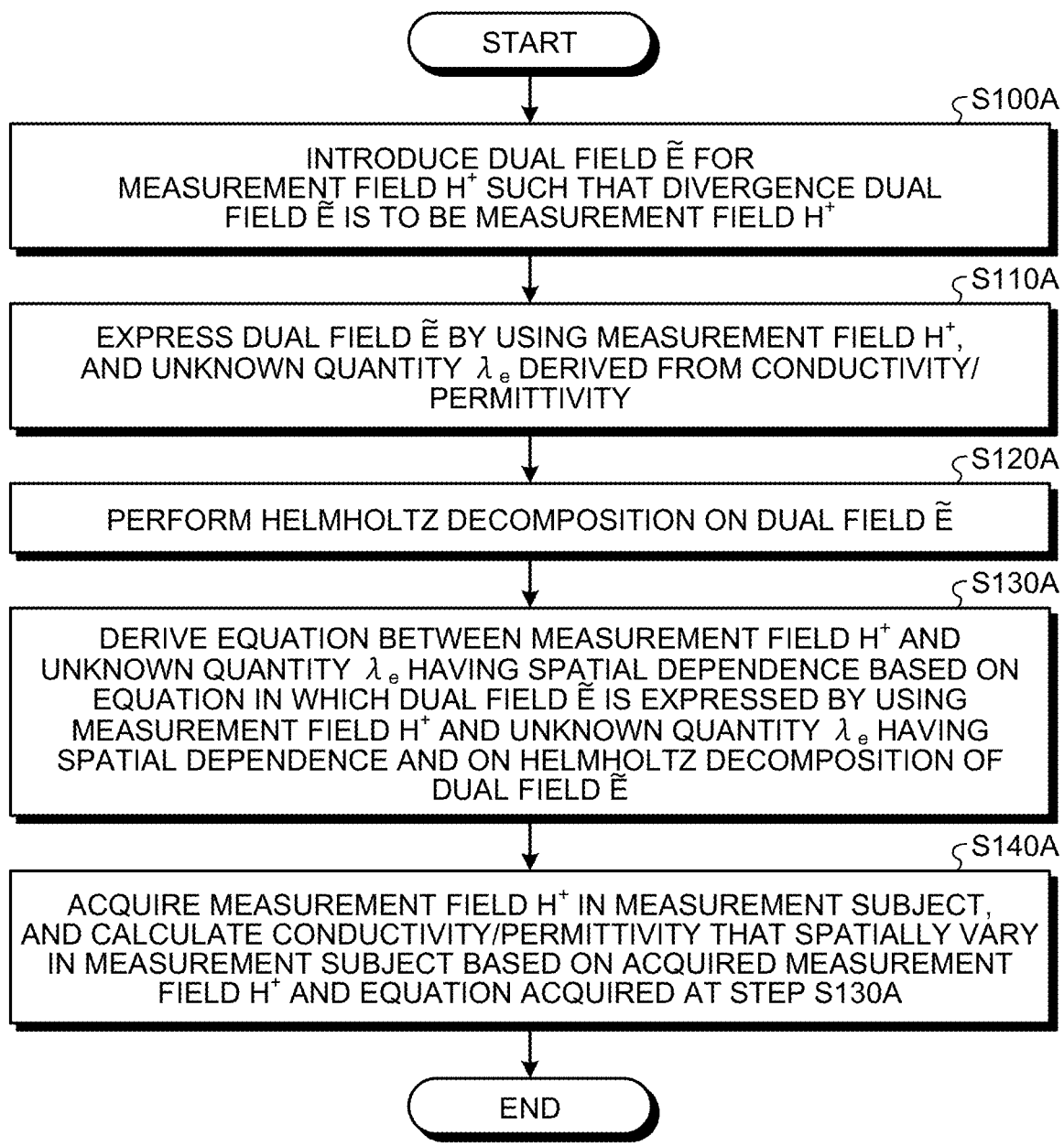

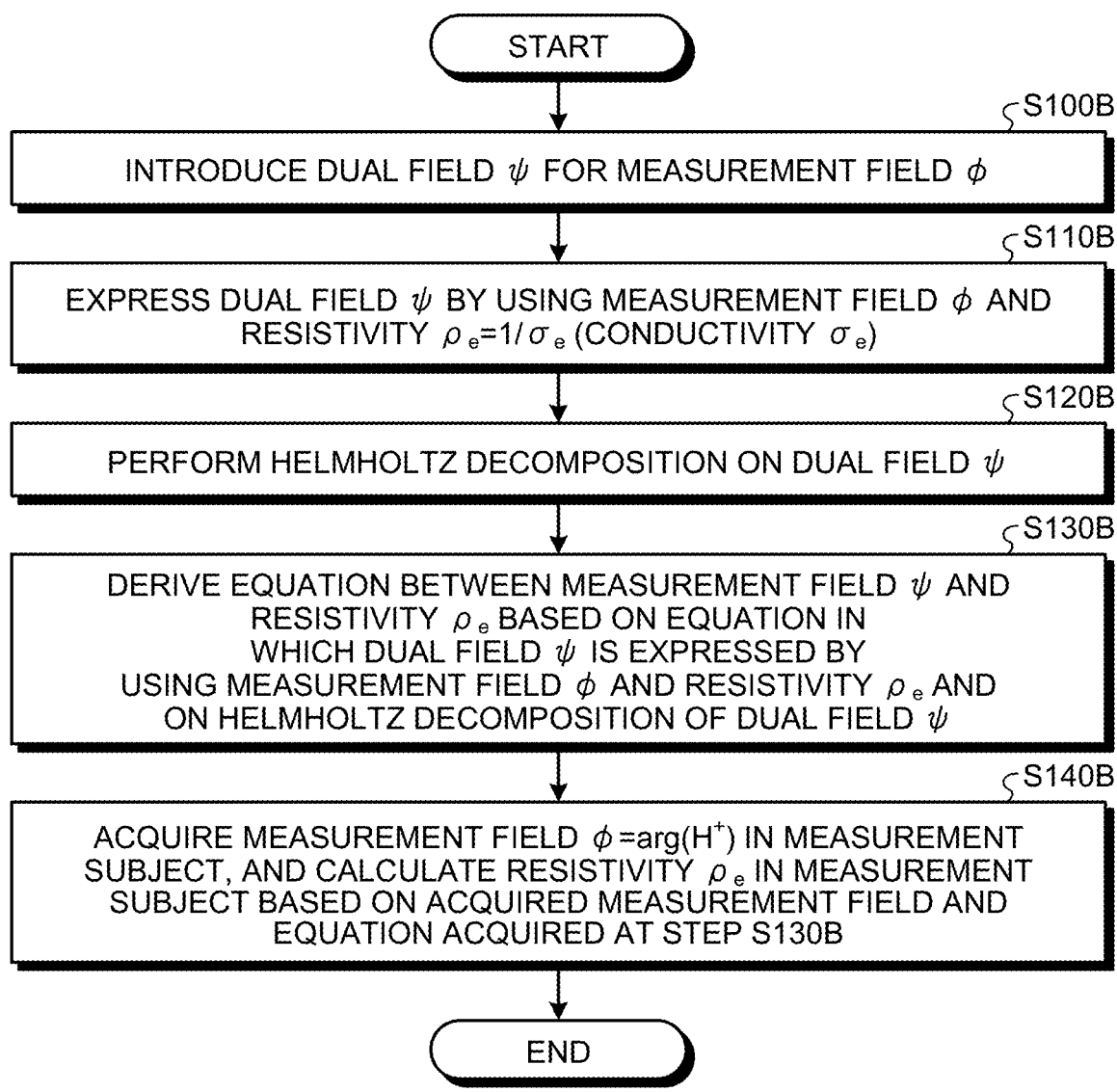

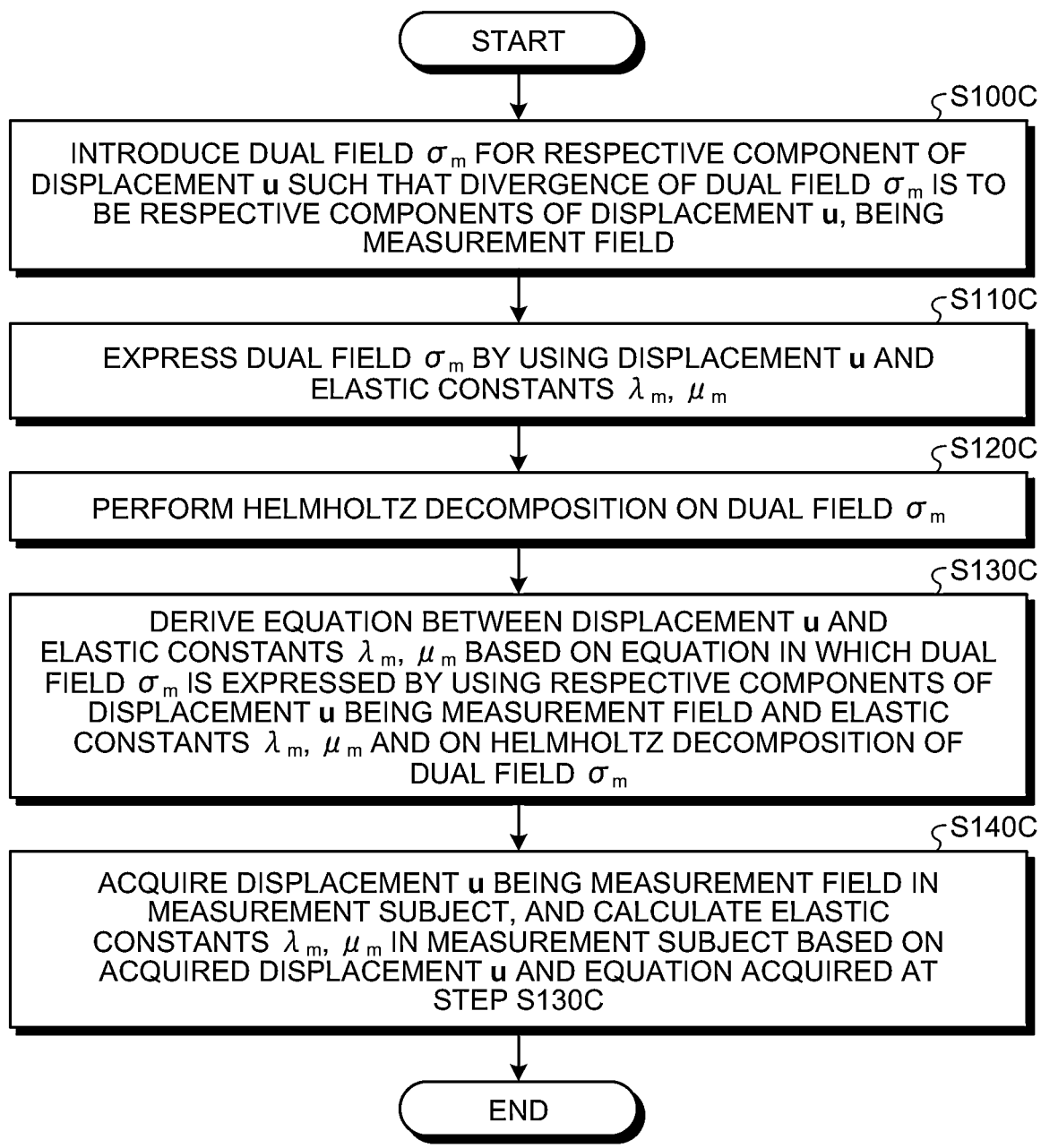

FIG.6

|  | 1. MREPT (Magnetic Resonance Electrical Property Tomography) | 2. QCM (Quantitative Conductivity Mapping) | 3. MRE (Magnetic Resonance Elastography) |
|---|---|---|---|
| BASIC EQUATION | FARADAY'S LAW $\nabla \times E = -i\omega\mu_0 H$<br>AMPERE'S LAW $E = \lambda_e \nabla \times H$ |  | EQUATION OF MOTION $\nabla \cdot \sigma_m = -\omega_1^2 \rho_m u$<br>HOOKE'S LAW $\sigma_m = \lambda_m \nabla \cdot u\, I + \mu_m (\nabla u + (\nabla u)^T)$ |
| MEASURE-MENT FIELD | RF MAGNETIC FIELD $H^+ = (H_x + iH_y)/2$ | PHASE OF $H^+$ $\phi = \arg H^+$ | DISPLACEMENT $u$ |
| UNKNOWN QUANTITY TO BE ESTIMATED | CONDUCTIVITY, PERMITTIVITY $\lambda_e = 1/(\sigma_e + i\omega\epsilon)$ | RESISTIVITY (CONDUCTIVITY) $\rho_e = 1/\sigma_e$ | ELASTIC CONSTANT $\lambda_m, \mu_m$ |

FIG.7

|  | 1. MREPT | 2. QCM | 3. MRE |
|---|---|---|---|
| (1) MEASUREMENT FIELD | $H^+ = (H_x + iH_y)/2$ | $\phi = \arg H^+$ | $u$ |
| (2) DUAL FIELD | $\tilde{E} = (iE_z/2, -E_z/2, -iE^+)^T$ | $\psi$ | $\sigma_m$ |
| (3) EXPRESS div OF DUAL FIELD USING MEASUREMENT FIELD | $\nabla \cdot \tilde{E} = i\omega\mu_0 H^+$ | $\nabla \cdot \psi = 2\omega\mu_0 \phi^0$ | $\nabla \cdot \sigma_m = -\omega_1^2 \rho_m u$ |
| (4) EXPRESS DUAL FIELD USING MEASUREMENT FIELD AND UNKNOWN QUANTITY | $\tilde{E} = \lambda_e \nabla_c H^+$ | $\psi = \rho_e \nabla \phi$ | $\sigma = \lambda_m \nabla \cdot u\, I + \mu_m (\nabla u + (\nabla u)^T)$ |

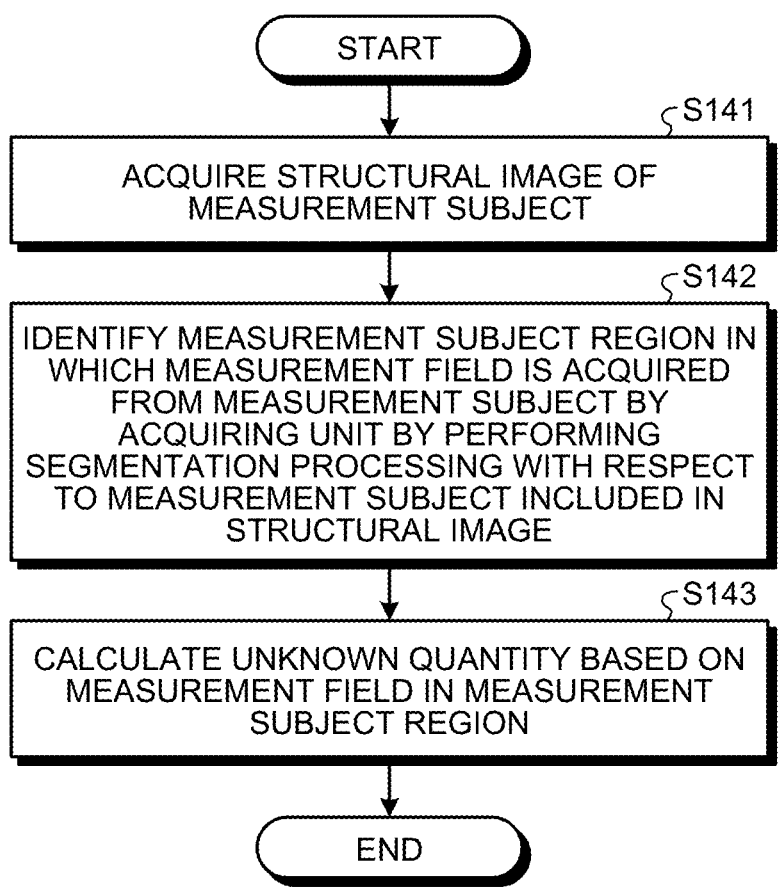

INFORMATION PROCESSING APPARATUS AND INFORMATION PROCESSING METHOD

CROSS-REFERENCE TO RELATED APPLICATIONS

This application is based upon and claims the benefit of priority from Japanese Patent Application No. 2021-011545, filed on Jan. 27, 2021; and Japanese Patent Application No. 2022-009328, filed on Jan. 25, 2022; the entire contents of which are incorporated herein by reference.

FIELD

Embodiments described herein relate generally to an information processing apparatus and an information processing method.

BACKGROUND

In medical image processing apparatuses, it is sometimes the case to provide new diagnostic information. For example, unlike normal structural images that are acquired by a X-ray CT apparatus and an MRI apparatus, it is sometimes the case to calculate and visualize a three dimensional distribution of unknown quantities in a human body, such as electric characteristics composed with conductivity and permittivity, or mechanical characteristics composed with a coefficient of elasticity and a coefficient of viscosity.

Examples of such a technique include magnetic resonance electrical property tomography (MREPT), quantitative conductivity mapping (QCM), magnetic resonance elastography (MRE), and the like. These make it possible to measure, for example, cancer, hepatic cirrhosis, and the like, as a change in physical property constant.

Assuming that electrical and mechanical characteristics change slowly inside the body of a human (mathematically, locally uniform), there has been a case in which characteristic values thereof are calculated and visualized. However, in this case, a large estimation error can occur at a boundary of an abnormal tissue. For example, in the case of MREPT, the estimation accuracy can be reduced when the conductivity discontinuously changes between a normal tissue and abnormal tissue, such as a localized solid cancer.

Moreover, there is also a case of considering spatial dependence of electrical and mechanical characteristics by a method using a finite element method or a method using integral representation of an electromagnetic field. However, for example, because a higher derivative of a measurement field is included in a differential equation to be solved, it can be an ill-posed problem, or because a differential equation to be solved is a non-linear equation with respect to unknown quantities, an iterative method is necessary to solve the differential equation, and it can often run into a local optimal solution unless an appropriate initial solution is given.

BRIEF DESCRIPTION OF THE DRAWINGS

FIG. 1 is a diagram illustrating a magnetic resonance imaging apparatus that includes an information processing apparatus 130 according to an embodiment;

FIG. 2 is a flowchart explaining a flow of processing that is performed by the information processing apparatus 130 according to the embodiment;

FIG. 3 is a flowchart explaining a flow of processing that is performed by the information processing apparatus 130 according to the embodiment in a case of MREPT;

FIG. 4 is a flowchart explaining a flow of processing that is performed by the information processing apparatus 130 according to the embodiment in a case of QCM;

FIG. 5 is a flowchart explaining a flow of processing that is performed by the information processing apparatus 130 according to the embodiment in a case of MRE;

FIG. 6 is a diagram explaining processing that is performed by the information processing apparatus 130 according to the embodiment;

FIG. 7 is a diagram explaining processing that is performed by the information processing apparatus 130 according to the embodiment;

FIG. 8 is a flowchart explaining the processing that is performed by the information processing apparatus 130 according to the embodiment.

DETAILED DESCRIPTION

Figure 9:
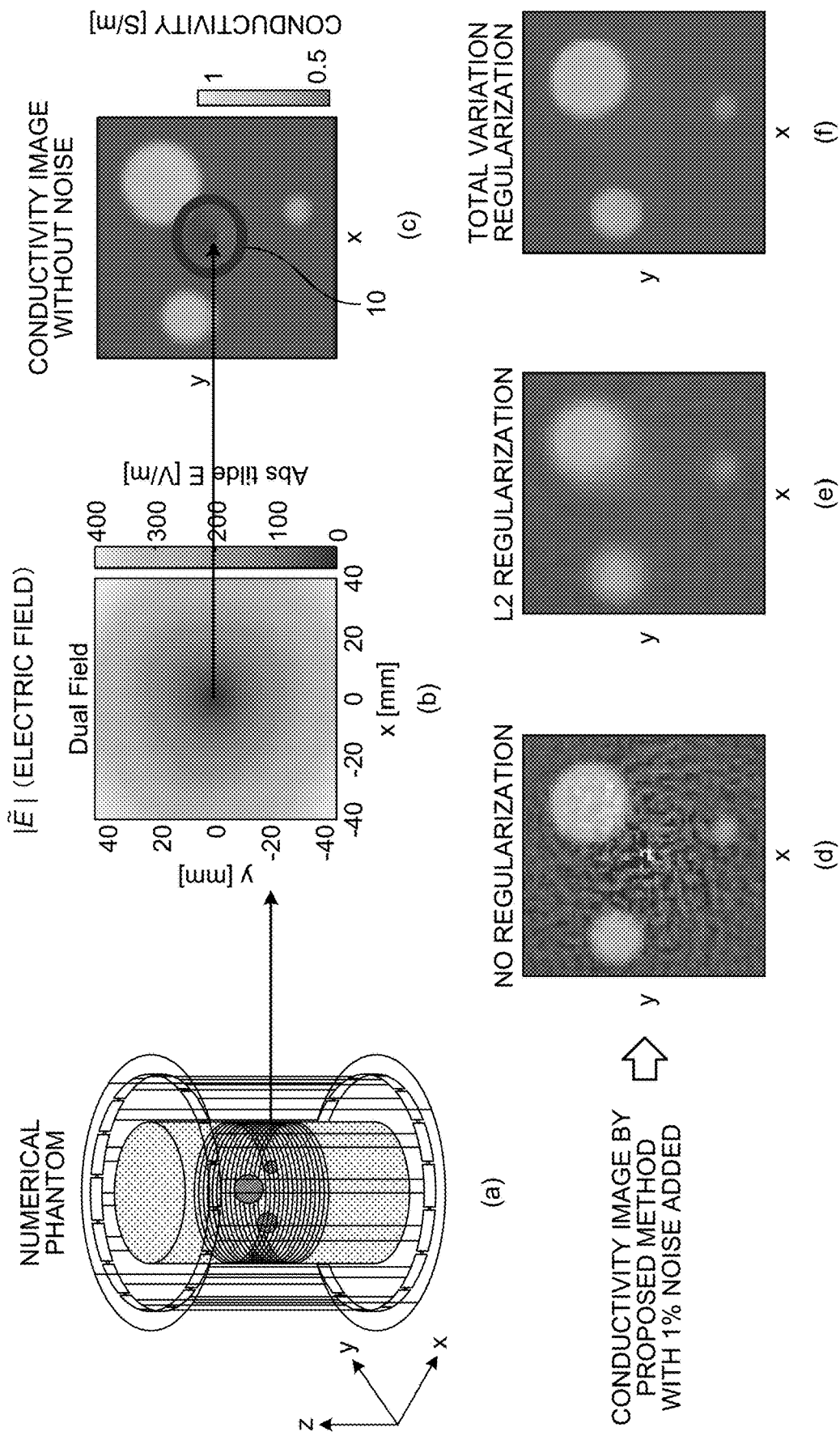
FIG. 9 is a flowchart explaining the processing that is performed by the information processing apparatus 130 according to the embodiment.

An information processing apparatus provided in one aspect of the present invention includes a processing circuit. The processing circuit acquires a measurement field corresponding to a spatial distribution of a predetermined physical quantity of a subject of measurement. The processing circuit calculates an unknown quantity of the subject of measurement based on a first equation between the measurement field and the unknown quantity that has spatial dependence therewith, and on the measurement field acquired by the acquiring unit. The first equation is one that is acquired based on a second equation expressing a dual field, divergence of which is capable of being expressed using the measurement field, in terms of the measurement field and the unknown quantity, and on the Helmholtz decomposition of the dual field.

Hereinafter, an embodiment of the information processing apparatus and an information processing method according to the embodiment will be explained with reference to the drawings.

FIG. 1 is a diagram illustrating a configuration when an information processing apparatus 130 according to the embodiment is included in a magnetic resonance imaging apparatus 100. However, the embodiment is not limited to a case in which the information processing apparatus 130 is included in the magnetic resonance imaging apparatus 100. The information processing apparatus 130 may be configured to be independent from the magnetic resonance imaging apparatus 100. Moreover, the information processing apparatus 130 may be included in a modality apparatus other than the magnetic resonance imaging apparatus 100, such as an ultrasound diagnostic apparatus. For example, in the following embodiment, a case of MRE that performs measurement of an elastic field by directly vibrating a tissue with a vibration plate or the like by using the magnetic resonance imaging apparatus 100 will be explained, but the embodiment is also applicable to various kinds of modalities capable of measuring an elasticity distribution by using a device that performs vibration measurement by directly vibrating a tissue for measurement of an elastic field, or the like.

As illustrated in FIG. 1, the magnetic resonance imaging apparatus 100 includes a static magnetic field magnet 101, a static magnetic field power supply (not illustrated), a gradient magnetic field coil 103, a gradient magnetic field power supply 104, a bed 105, a bed control circuit 106, a transmitter coil 107, a transmitter circuit 108, a receiver coil 109, a receiver circuit 110, a sequence control circuit 120 (sequence control unit), and the information processing apparatus 130. Note that a subject P (for example, human body) is not included in the magnetic resonance imaging apparatus 100. Furthermore, the configuration illustrated in FIG. 1 is only one example. For example, respective components in the sequence control circuit 120 and the information processing apparatus 130 may be configured to be integrated or separated as appropriate.

The static magnetic field magnet 101 is a magnet formed in a substantially cylindrical shape having a hollow, and generates a static magnetic field in space inside the cylinder in a central axis (Z-axis) direction. The static magnetic field magnet 101 is, for example, a superconducting magnet or the like, and is magnetized, receiving a supply of an electric current from the static magnetic field power supply. The static magnetic field power supply supplies an electric current to the static magnetic field magnet 101. As another example, the static magnetic field magnet 101 may be a permanent magnet, and in this case, the static magnetic field power supply may be excluded in the magnetic resonance imaging apparatus 100. Moreover, the static magnetic field power supply may be provided separately from the magnetic resonance imaging apparatus 100.

The gradient magnetic field coil 103 is a coil formed in a substantially cylindrical shape having a hollow, and is arranged inside the static magnetic-field magnet 101. The gradient magnetic field coil 103 is formed with three coils corresponding to respective axes of X, Y, and Z that are perpendicular to one another combined, and these three coils generate a gradient magnetic field, a magnetic field strength of which varies according to a distance from the center of the respective axes along the respective axes of X, Y, and Z, receiving a supply of an electric current individually from the gradient magnetic field power supply 104. Magnetic fields of the respective axes of X, Y, and Z generated by the gradient magnetic field coil 103 are, for example, a gradient magnetic field Gs for slicing, a gradient magnetic field Ge for phase encoding, and a gradient magnetic field Gr for readout. The gradient magnetic field power supply 104 supplies an electric current to the gradient magnetic field coil 103.

The bed 105 includes a table 105a on which the subject P is laid, and inserts the table 105a into the hollow (imaging port) of the gradient magnetic field coil 103 in a state in which the subject P is laid thereon, under control of the bed control circuit 106. Normally, the bed 105 is arranged such that a longitudinal direction thereof is parallel to the central axis of the static magnetic field magnet 101. The bed control circuit 106 drives the bed 105 to move the table 105a in a longitudinal direction and a vertical direction, under control of the information processing apparatus 130.

The transmitter coil 107 is arranged inside the gradient magnetic-field coil 103, and receives a supply of a radio frequency (RF) pulse from the transmitter circuit 108 to generate a high frequency magnetic field. The transmitter circuit 108 supplies an RF pulse corresponding to the Larmor frequency determined by a kind of atom to be a subject and a magnetic field strength.

The receiver coil 109 is arranged inside the gradient magnetic field coil 103, and receives a magnetic resonance signal (hereinafter, referred to as "MR signal" as necessary) emitted from the subject P due to an influence of the high frequency magnetic field. Having received the magnetic resonance signal, the receiver coil 109 outputs the received magnetic resonance signal to the receiver circuit 110.

Note that the transmitter coil 107 and the receiver coil 109 described above are only one example. It may be configured by combining one or more of a coil having only a transmitter function, a coil having only a receiver function, and a coil having transmitter and receiver functions.

The receiver circuit 110 detects a magnetic resonance signal output from the receiver coil 109, and generates magnetic resonance data based on the detected magnetic resonance signal. Specifically, the receiver circuit 110 generates the magnetic resonance data by subjecting the magnetic resonance signal output from the receiver coil 109 to digital conversion. Moreover, the receiver circuit 110 transmits the generated magnetic resonance data to the sequence control circuit 120. The receiver circuit 110 may be provided in a frame unit that includes the static magnetic field magnet 101, the gradient magnetic-field coil 103, and the like.

The sequence control circuit 120 drives the gradient magnetic field power supply 104, the transmitter circuit 108, and the receiver circuit 110 based on sequence information transmitted from the information processing apparatus 130, and thereby performs imaging of the subject P. The sequence information is information in which a procedure to perform imaging is defined. The sequence information defines strength of an electric current to be supplied to the gradient magnetic field coil 103 by the gradient magnetic field power supply 104 and timing of supplying the electric current, strength of an RF pulse to be supplied to the transmitter coil 107 by the transmitter circuit 108, and timing of applying the RF pulse, timing of detecting the magnetic resonance signal by the receiver circuit 110, and the like. For example, the sequence control circuit 120 is an integrated circuit, such as an application specific integrated circuit (ASIC) and a field programmable gate array (FPGA), or an electronic circuit, such as a central processing unit (CPU) and a micro processing unit (MPU). Details of a pulse sequence performed by the sequence control circuit 120 will be described later.

Furthermore, when the sequence control circuit 120 receives magnetic resonance data from the receiver circuit 110 as a result of imaging the subject P by driving the gradient magnetic field power supply 104, the transmitter circuit 108, and the receiver circuit 110, the sequence control circuit 120 transfers the received magnetic resonance data to the information processing apparatus 130. The information processing apparatus 130 performs overall control of the magnetic resonance imaging apparatus 100, generation of an image, and the like. The information processing apparatus 130 includes a memory 132, an input device 134, a display 135, and a processing circuit 150. The processing circuit 150 includes an interface function 131, a control function 133, and a generating function 136.

In the embodiment, respective processing functions performed by the interface function 131, the control function 133, the generating function 136, an identifying function 137, an acquiring function 138, and a calculating function 139 are stored in the memory 132 in a form of computer-executable program. The processing circuit 150 is a processor that reads out a program from the memory 132, and implements functions corresponding to the respective programs. In other words, the processing circuit 150 that has read the respective programs is to have the respective functions illustrated in the processing circuit 150 in FIG. 1. In FIG. 1, it has been explained that the processing functions performed by the control function 133, the generating function 136, the identifying function 137, the acquiring function 138, and the calculating function 139 are implemented by a single unit of the processing circuit 150, but the processing circuit 135 may be configured by combining plural independent processors, and it may be configured to implement the respective functions by executing the programs by the respective processors. In other words, the respective functions described above may be configured as programs, and one unit of the processing circuit 150 may execute the respective programs. As another example, a specific function may be implemented in an independent dedicated program execution circuit. In FIG. 1, the interface function 131, the control function 133, the generating function 136, the identifying function 137, the acquiring function 138, and the calculating function 139 are one example of an accepting unit, a control unit, a generating unit, an identifying unit, an acquiring unit, and a calculating unit, respectively. Moreover, the sequence control circuit 120 is one example of a sequence control unit. Specific processing of the identifying function 137, the acquiring function 138, and the calculating function 139 will be described later.

A term "processor" used in the above explanation signifies a circuit, such as a CPU, a graphical processing unit (GPU), an ASIC, a programmable logic device (for example, simple programmable logic device (SPLD), complex programmable logic device (CPLD)), and a field programmable gate array (FPGA). The processor implements a function by reading and executing a program stored in the memory 132.

Moreover, instead of storing a program in the memory 132, it may be configured to directly install a program in a circuit of the processor. In this case, the processor reads and executes the program installed in the circuit, to implement the function. The bed control circuit 106, the transmitter circuit 108, the receiver circuit 110, and the like are configured similarly by an electronic circuit such as the processor described above.

The processing circuit 150 transmits sequence information to the sequence control circuit 120, and receives magnetic resonance data from the sequence control circuit 120 by the interface function 131. Furthermore, having received magnetic resonance data, the processing circuit 150 having the interface function 131 stores the received magnetic resonance data in the memory 132.

The magnetic resonance data stored in the memory 132 is arranged in k-space by the control function 133. As a result, the memory 132 stores k-space data.

The memory 132 stores magnetic resonance data received by the processing circuit 150 having the interface function, k-space data that is arranged in k-space by the processing circuit 150 having the control function, image data generated by the processing circuit 150 having the generating function 136, and the like. The memory 132 is, for example, a semiconductor memory device, such as a random access memory (RAM) and a flash memory, a hard disk, an optical disk, or the like.

The input device 134 accepts various kinds of instruction or data input by an operator. The input device 134 is, for example, a pointing device such as a mouse and a trackball, a selecting device such as a mode switch, or a input device such as a keyboard. The display 135 displays a graphical user interface (GUI) to accept an input of an imaging condition under control of the processing circuit 150 having the control function 133, an image that is generated by the processing circuit 150 having the generating function 136, and the like. The display 135 is a display device, such as a liquid crystal display, for example.

The processing circuit 150 controls overall operation of the magnetic resonance imaging apparatus 100 by the control function 133, and controls imaging, generation of an image, display of an image, and the like. For example, the processing circuit 150 having the control function 133 accepts an input of an imaging condition (imaging parameter, and the like) on the GUI, and generates sequence information according to the accepted imaging condition. Moreover, the processing circuit 150 having the control function 133 transmits the generated sequence information to the sequence control circuit 120.

The processing circuit 150 reads out the k-space data from the memory 132, and subjects the read k-space data to reconstruction processing, such as Fourier transform by using the generating function 136, to generate an image.

Subsequently, the background of the embodiment will be explained.

In medical image processing apparatuses, it is sometimes the case to provide new diagnostic information different from a normal X-ray CT apparatus and an MRI apparatus. For example, unlike normal structural images that are acquired by an X-ray CT apparatus and an MRI apparatus, it is sometimes the case to calculate and visualize a three dimensional distribution of these unknown quantities in a human body, such as electric characteristics composed with conductivity and permittivity, or mechanical characteristics composed with a coefficient of elasticity and a coefficient of viscosity. Examples of such a technique include MREPT, QCM, MRE, and the like. These make it possible to measure, for example, cancer, hepatic cirrhosis, and the like, as a change in physical property constant.

In the conventional techniques, assuming that electrical and mechanical characteristics change slowly inside the body of a human (mathematically, locally uniform), there has been a case in which those are calculated and visualized. However, a large estimation error can occur at a boundary of an abnormal tissue if electrical and mechanical characteristics are locally uniform inside the body of a human.

Moreover, it can be considered to take spatial dependence of electrical and mechanical characteristics into account by a method using a finite element method or a method using integral representation of an electromagnetic field. However, for example, because a higher derivative of a measurement field is included in a differential equation to be solved, it can be an ill-posed problem in the case of the former method, and in the case of the latter method, because a differential equation to be solved is a non-linear equation with respect to unknown quantities, an iterative method is necessary to solve the differential equation, and it can often run into a local optimal solution unless an appropriate initial solution is given.

In view of the background, the information processing apparatus 130 according to the embodiment uses integral representation to be robust against observation noise, introduces a dual field with respect to a measurement field such that an equation to be solved is an integral equation linear to unknown quantities, and calculates the unknown quantities having spatial dependence based on a equation derived from the Helmholtz decomposition of the dual field.

Specifically, the information processing apparatus 130 according to the embodiment includes the processing circuit 150. The processing circuit 150 acquires a measurement field corresponding to a spatial distribution of a predetermined physical quantity in a subject of measurement by using the acquiring function 138. Moreover, the processing circuit 150 calculates an unknown quantity in the subject of measurement based on a first equation between the measurement field and the unknown quantity having spatial dependence, by using calculating function 139. The first equation is one that is acquired based on a second equation expressing a dual field divergence of which is capable of being expressed using the measurement field, by using the measurement field and the unknown quantity, and on the Helmholtz decomposition of the dual field.

Furthermore, the information processing method according to the embodiment includes acquisition of a measurement field corresponding to spatial distribution of a predetermined physical quantity in the subject of measurement, and calculation of an unknown quantity in the subject of measurement based on the first equation between the measurement field and the unknown quantity having spatial dependence, and on the measurement field acquired by the acquiring unit, and the first equation is one that is acquired based on a second equation expressing a dual field divergence of which is capable of being expressed using the measurement field, by using the measurement field and the unknown quantity, and on the Helmholtz decomposition of the dual field.

According to the information processing apparatus 130 and the information processing method, an image quality can be improved.

Hereinafter, processing performed by the information processing apparatus according to the embodiment will be explained by using FIG. 2 to FIG. 7. FIG. 2 is a flowchart explaining a procedure of the processing performed by the information processing apparatus according to the embodiment. In FIG. 2, general terms of the procedure of the processing performed by the information processing apparatus according to the embodiment will be explained, and in FIG. 3 to FIG. 5, details of the processing when the procedure is applied will be explained in individual application cases. Specifically, FIG. 3 to FIG. 5 explain the procedure when the processing according to the embodiment is applied in examples of MREPT, QCM, and MRE specifically. FIG. 6 is a diagram explaining a relation among a measurement field, an unknown quantity to be estimated, and a basic equation, and FIG. 7 is a diagram explaining a measurement field, a dual field, and a relation between the measurement field and the dual field.

First, a relation between a measurement field and an unknown quantity in the information processing apparatus 130 according to the embodiment will be explained.

Explanation of step S100 to step S130 will be described later, and explanation of step S140 will be explained first. In FIG. 2, at step S140, the processing circuit 150 acquires a measurement field corresponding to a spatial distribution of a predetermined physical quantity in a subject of measurement by using the acquiring function 138, and calculates the unknown quantity of the subject of measurement based on the acquired measurement field and an equation acquired at step S130 by using the calculating function 139. Specifically, the processing circuit 150 acquires a measurement field corresponding to a spatial distribution of a predetermined physical quantity of the subject of measurement by using the acquiring function. Subsequently, the processing circuit 150 estimates an unknown quantity having spatial dependence of the subject of measurement based on the measurement field acquired by the acquiring function 138, and on a first equation between the measurement field and the unknown quantity having spatial dependence that is acquired at step S130 described later. The first equation is an equation derived from a basic equation. As described later, the first equation is one that is acquired based on a second equation expressing a dual field divergence of which is capable of being expressed using the measurement field, by using the measurement field and the unknown quantity, and on the Helmholtz decomposition of the dual field.

FIG. 6 illustrates a relation between these measurement field and unknown quantity according to the embodiment.

Examples of a first application of the embodiment include MREPT. MREPT is a method in which an amplitude and a phase of an RF magnetic field inside the body of a human are measured by using an MRI, and distributions of a conductivity and a permittivity are visualized.

In the case of MREPT, the processing circuit 150 acquires an RF magnetic field $H^+$ given by following Equation (1) as a measurement field by using the acquiring function 138.

$$H^+ = (H_x + iH_y)/2 \qquad (1)$$

$H_x$ and $H_y$ are an RF magnetic field in an x-axis and a y-axis directions that are respectively perpendicular to a z-axis.

Moreover, the Faraday's law given by following Equation (2) and the Ampere's rule given by following Equation (3) hold.

$$\nabla \times E = -i\omega\mu_0 H \qquad (2)$$

$$E = \lambda_e \nabla \times H \qquad (3)$$

E is an electric field, $\omega$ is a Larmor angular frequency, and $\mu_0$ is a permeability in vacuum, an H is an RF magnetic field. Moreover, $\lambda e$ is an impedance, and is given by following Equation (4).

$$\lambda e = 1/(\sigma_e + i\omega \in) \qquad (4)$$

$\sigma e$ is a conductivity, and $\varepsilon$ is a permittivity.

Moreover, in the case of MREPT, the processing circuit 150 estimates the conductivity $\sigma e$, the permittivity $\varepsilon$, or the impedance $\lambda e$ given by Equation (4), as an unknown quantity having spatial dependence by using the calculating function 139.

That is, in the case of MREPT, as indicated at step S140A in FIG. 3, the processing circuit 150 acquires an RF magnetic field $H^+$ given by Equation (1) as a measurement field by using the acquiring function 138. Subsequently, the processing circuit 150 calculates the conductivity $\sigma e$, the permittivity $\varepsilon$, or the impedance $\lambda e$ that is an unknown quantity spatially varying in the subject of measurement.

In other words, in the case of MREPT, the measurement field is an amplitude and a phase of the RF magnetic field $H^+$, and the unknown quantity spatially varying in the subject of measurement includes the conductivity $\sigma e$ and the permittivity $\varepsilon$. The processing circuit 150 performs MREPT based on the unknown quantity calculated by the calculating function 139.

An equation between the measurement field $H^+$ and the unknown quantity $\lambda e$ is derived based on Faraday's law given by Equation (2) and Ampere's law given by Expression (3). That is, the first equation is one that is derived from Ampere's law and Faraday's law.

In the following, a method of measuring the RF magnetic field $H^+$ in respective voxels of the subject of measurement will be briefly explained. First, an RF signal is transmitted to the transmitter coil 107 by the transmitter circuit 108 based on a spin echo (SE) sequence or a gradient echo (GRE) sequence performed by the sequence control circuit 120. The processing circuit 150 acquires an SE signal or a GRE signal acquired from the acquiring function 138 from the receiver coil 109 through the receiver circuit 110.

Because the RF magnetic field $H^+$ is a complex number, basically, the magnetic resonance imaging apparatus 100 according to the embodiment is to perform measurement of an amplitude and a phase of an RF magnetic field.

As for measurement of an amplitude of an RF magnetic field, some kinds of methods are known, and it is generally called B1 mapping. As a basic principle, when a signal strength (amplitude) is S, magnetization at a position (x, y, z) is M0, and a flip angle at which the magnetization inclines by an RF pulse is α, S=M0(x, y, z)sin α holds. Therefore, the signal strength (amplitude) is proportional to sin α, where the flip angle at which the magnetization inclines by an RF pulse is α. Therefore, the processing circuit 150 can calculate the flip angle α by the calculating function 139, and can calculate an amplitude of the RF magnetic field by calculating sin α based on the calculated flip angle α.

As one example of measurement of an amplitude of the RF magnetic field, to remove an influence of repetition time in the GRE sequence and longitudinal relaxation time (T1) of the subject of measurement, the sequence control circuit 120 performs pulse sequence of the GRE method at two flip angles (hereinafter, α and α2). The processing circuit 150 generates images by the GRE method for the two flip angles based on the pulse sequence performed by the sequence control circuit 120. Because r=sin α/sin 2α=½ cos α is given when a ratio of the signal strength per voxel is r, the processing circuit 150 can calculate the flip angle α based on the ratio r of the signal strength per voxel that is acquired from an image generated for the two flip angles, and measures an amplitude of an RF magnetic field by acquiring sin α based on this.

Furthermore, as for measurement of a phase of an RF magnetic field, for example, a method in which the sequence control circuit 120 performs a pulse sequence of the SE method, and a transmission RF phase is measured based on a phase image at a peak time of an SE signal from the subject of measurement by the calculating function 139 is considered. An example of using a quadrature birdcage coil for transmission and reception of an RF magnetic field will be explained herein. This coil is known to generate a significantly uniform RF magnetic field in free space (for example, Convection-Reaction Equation Based Magnetic resonance Electrical Properties Tomography (cr-MREPT): IEEE Transactions on Medical Imaging, Vol. 33, No. 3, March 2014 777). When an SE image is acquired by this coil, an SE image is acquired by positioning an echo peak at the center of k-space, to be subjected to Fourier transform. Because it is an SE image, a phase caused by nonuniformity of static magnetic field is canceled, but a phase caused by an eddy current magnetic field generated by driving of the RF transmitter/receiver and a gradient magnetic field remains, and is expressed as in following Equation (5).

$$\phi(r)=\phi_+(r)+\phi_-(r)+\int \gamma Be(r)dt \qquad (5)$$

φ(r) is a phase of an SE image, r is a position, and φ+(r) is a phase of a transmission RF magnetic field, φ−(r) is a phase at the time of reception, and ∫γBe(r)dt is a phase caused by an eddy current magnetic field. The latter can be canceled by performing subtraction processing with a phase of an SE image that is obtained by inverting a gradient magnetic field by the same SE sequence, and φ+(r)+φ−(r) can be acquired. On the other hand, it is known that φ+(r) and φ−(r) are substantially equal to each other. Accordingly, the transmission RF phase φ+(r) desired to be acquired can be acquired by (φ+(r)+φ−(r))/2. Although the measuring method of an amplitude and a phase of an RF magnetic field has been explained, a scope of the present invention is not limited to use this measuring method. As long as it is a method of acquiring information about an amplitude and a phase, other measuring methods or estimating methods may be used.

As a second application example of the embodiment, QCM is considered. QCM is a method in which a distribution of a conductivity is visualized, based only on a phase distribution of an RF magnetic field.

In the case of QCM, the processing circuit 150 acquires a measurement field φ given by following Equation (6) by using the acquiring function 138.

$$\phi=\arg H^+ \qquad (6)$$

More specifically, the processing circuit 150 acquires the measurement field φ by extracting a phase component of the RF magnetic field $H^+$ by using the acquiring function 138.

Moreover, in the case of QCM, the processing circuit 150 estimates a conductivity σe, or a resistivity ρe given by Equation (7) as an unknown quantity having spatial dependence by using the calculating function 139.

$$\rho_e=1/\sigma_e \qquad (7)$$

That is, in the case of QCM, as indicated at step S140B in FIG. 4, the processing circuit 150 acquires the measurement field φ given by Equation (6) by the acquiring function 138. Subsequently, the processing circuit 150 calculates the conductivity σe or the resistivity ρe that is an unknown quantity spatially varying in the subject of measurement, based on the first equation between the measurement field φ and the unknown quantity ρe having spatial dependence, acquired at step S130B.

In other words, in the case of QCM, a measurement field is the phase φ of the RF magnetic field $H^+$, and the unknown quantity spatially varying in the subject of measurement includes the conductivity σe or the resistivity ρe. The processing circuit 150 performs QCM based on the unknown quantity calculated by the calculating function 139.

The first equation between the measurement field φ and the resistivity ρe is derived with assumptions that spatial variation of an amplitude of $H^+$ is slow and σe>>ωε in Faraday's law given by Equation (2) and in Ampere's law given by Equation (3) used in the case of MREPT.

As a third application example of the embodiment, MRE can be considered. MRE is a method in which displacement distribution when vibration is applied from outside of a human body is measured by using MRI, and a distribution of a coefficient of elasticity and a coefficient of viscosity inside the human body is visualized.

In the case of MRE, the processing circuit 150 acquires a displacement u as a measurement field by using the acquiring function 138. The displacement u is a vector quantity.

Moreover, an equation of motion given by following Equation (8) and Hooke's law given by following Equation (9) hold.

$$\nabla \cdot \sigma_m = -\omega_1^2 \rho_m u \qquad (8)$$

$$\sigma_m = \lambda_m \nabla \cdot u I + \mu_m (\nabla u + (\nabla u)^T) \qquad (9)$$

σm is a stress, $\omega_1$ is an angular frequency of vibration, ρm is a density, and u is a displacement. Because the stress σm is a tensor quantity and the displacement u is a vector quantity, Equation (8) indicates that what is acquired by multiplying respective components of the displacement u by $-\omega_1^2$σm is equal to divergence of a vector that is each line or column of the stress σm extracted. Furthermore, λm and μm are coefficients of elasticity, and specifically, λm is a first Lamé's constant, and μm is a second Lamé's constant. Moreover, I indicates a unit matrix.

Furthermore, in the case of MRE, the processing circuit 150 estimates elastic constants λm and μm, that is, the coefficient of elasticity and the coefficient of viscosity as an unknown quantity having spatial dependence by using the calculating function 139.

That is, in the case of MRE, as indicated at step S140C in FIG. 5, the processing circuit 150 acquires the displacement u as a measurement field by using the acquiring function 138.

Subsequently, the processing circuit 150 calculates the elastic constants λm and μm that are unknown quantities spatially varying in the subject of measurement, or a coefficient of elasticity, a coefficient of viscosity, and the like based on those elastic constants, based on the displacement u, which is the measurement field, and on the first equation between the displacement u acquired at step S130C and the elastic constants λm and μm.

In other words, in the case of MRE, the measurement field is the displacement u, and the unknown quantity spatially varying in the subject of measurement includes a coefficient of elasticity and a coefficient of viscosity. The processing circuit 150 performs MRE based on the unknown quantity calculated by the calculating function 139.

The first equation between the displacement u which is the measurement field, and the elastic constants λm and μm is derived based on the equation of motion expressed by Equation (8) and the Hooke's law given by Equation (9). That is, the first equation is one derived from the equation of motion of an elastic body and the Hooke's law.

Subsequently, returning back to FIG. 2, step S100 and step S110 in FIG. 2 will be explained, referring to FIG. 7 as necessary.

First, at step S100, a dual field, divergence of which is capable of being expressed using a measurement field, is introduced for the measurement field. Furthermore, at step S110, the dual field introduced at step S100 is expressed by using the measurement field and the unknown quantity having spatial dependence. That is, at step S110, the second equation in which the dual field, divergence of which is capable of being expressed using a measurement field, is expressed by using the measurement field and the unknown quantity having spatial dependence is introduced.

In the case of MREPT, for example, a field E (quantity that is expressed with a tilde) that satisfies following Equation (10) is introduced.

$$\tilde{E} \equiv (iE_z/2, -E_z/2, -iE^+)^T \quad (10)$$

$E_x$, $E_y$, and $E_z$ are components in the x-axis, the y-axis, and the z-axis directions of electric field, respectively, and $E^+ = (E_x + i E_y)/2$.

Moreover, by transforming Equation (2), which is the Faraday's law, following Equation (11) is acquired.

$$\nabla \cdot \tilde{E} = i\omega\mu_0 H^+ \quad (11)$$

That is, the divergence of the field E (quantity that is expressed with a tilde) on a left side of Equation (11) is constant multiplication of the measurement field, and the divergence is expressed by the measurement field $H^+$. Therefore, the field E (quantity that is expressed with a tilde) on the left side of Equation (11) is to be expressed by the measurement field $H^+$, and is to be a dual field to the measurement field $H^+$.

That is, in the case of MREPT, as illustrated in FIG. 3, at step S100A, the dual field E (quantity that is expressed with a tilde) is introduced for the measurement field $H^+$ such that the divergence of the dual field E (quantity that is expressed with a tilde) is to be the measurement field $H^+$.

Moreover, by transforming Equation (3), which is the Ampere's law, following Equation (12) is acquired.

$$\tilde{E} = \lambda_e \nabla_c H^+ \quad (12)$$

An operator $\nabla c$ is an operator that is defined by following Equation (13).

$$\nabla_c \equiv \begin{pmatrix} \partial_x - i\partial_y \\ i(\partial_x - i\partial_y) \\ \partial_z \end{pmatrix} = \begin{pmatrix} 2\partial \\ 2i\partial \\ \partial_z \end{pmatrix} \quad (13)$$

That is, in Equation (12), the dual field E (quantity that is expressed with a tilde) is expressed by using the measurement field $H^+$ and the unknown quantity $\lambda_e$ having spatial dependence.

That is, at step S110A, the dual field E (quantity that is expressed with a tilde) is expressed by using the measurement field $H^+$, the unknown quantity $\lambda_e$ that is derived from conductivity $\sigma_e$/permittivity ε.

In the case of QCM, to the measurement field $H^+$ expressed by Equation (5), the field φ that satisfies, for example, following Equation (14) is introduced as the dual field for the measurement field φ.

$$\nabla \cdot \psi = 2\omega\mu_0 \phi^0 \quad (14)$$

That is, in the case of QCM, as illustrated in FIG. 4, at step S100B, the dual field ψ is introduced for the measurement field φ such that the divergence of the dual field ψ is zero power of the measurement field $\phi = \arg(H^+)$, that is, to be proportional to the constant.

Moreover, similarly to the case of MREPT, by transforming the basic equation, following Equation (15) is acquired.

$$\psi = \rho_e \nabla \phi \quad (15)$$

That is, in Equation (15), the dual field ψ is expressed by using the measurement field φ and the unknown quantity $\rho_e$ having spatial dependence.

That is, in the case of QCM, as illustrated in FIG. 4, at step S110B, the dual field ψ is expressed by using the unknown quantity derived from the measurement field φ and the resistivity ρe (conductivity $\sigma_e$).

In the case of MRE, for example, a field $\sigma_m$ that satisfies following Equation (16) is introduced.

$$\nabla \cdot \sigma_m = -\omega_1^2 \rho_m u \quad (16)$$

Comparing Equation (16) with Equation (8), which is an equation of motion, the field $\sigma_m$ of the left side of Equation (16) is a stress tensor. The divergence of the field $\sigma_m$ of the left side of Equation (16) is to be an expression using the measurement field u. Accordingly, because the divergence of the field $\sigma_m$ of the left side of the Equation (16) is to be expressed with the measurement field u, it is to be a dual field with respect to the measurement field u. That is, the stress tensor $\sigma_m$ in MRE is to be a dual field.

In Equation (16), $\rho_m$ is a density of an elastic body, $\omega_1$ is an angular frequency of vibration externally applied. Moreover, in Equation (16), the dual field $\sigma_m$ is a tensor quantity, and the measurement field u is a vector quantity, but similarly to Equation (8), Equation (16) indicates that the divergence of respective line vectors or respective column vectors of the dual field $\sigma_m$ is equal to each component of the measurement field u.

That is, in the case of MRE, as illustrated in FIG. 5, at step S100C, the dual field $\sigma_m$ is introduced for respective components of the displacement u such that the divergence of (respective line or column vectors of) the dual field $\sigma_m$ is to be the respective components of the displacement u, which is the measurement field.

Furthermore, Equation (9), which is Hooke's law, is to be an equation in which the dual field $\sigma_m$ is expressed, with the elastic constants $\lambda_m$ and $\mu m$ being unknown quantities to be estimated, by using the measurement field u and the unknown quantity having spatial dependence, as indicated in following Equation (17) as described below.

$$\sigma_m = \lambda_m \nabla \cdot u I + \mu_m (\nabla u + (\nabla u)^T) \quad (17)$$

That is, as illustrated in FIG. 5, at step S110C, the dual field $\sigma_m$ is expressed by using the measurement field u and the elastic constants $\lambda_m$ and $\mu_m$, which are unknown quantities.

Returning back to FIG. 2, at step S120, Helmholtz decomposition of the dual field is performed. Helmholtz decomposition is an operation of expressing a three-dimensional vector field as a sum of a field with a rotation-free vector field and a divergence-free vector field by using Helmholtz's theorem. According to Helmholtz's theorem, it has been known that a three-dimensional vector field can be expressed as a sum of a rotation-free vector field and a divergence-free vector field. Following Equation (18) expresses Helmholtz decomposition of any three-dimensional vector field f(r') inside a bounded region of interest $\Omega$.

$$f(r') = \left( \int_\Omega (\nabla \cdot f) \nabla \frac{1}{4\pi |r'-r|} dv - \int_{\partial\Omega} (n \cdot f) \nabla \frac{1}{4\pi |r'-r|} dS \right) + \int_\Omega (f \times \nabla) \times \nabla \frac{1}{4\pi |r'-r|} dv \quad (18)$$

r and r' indicate a position, dv is a volume element in the region of interest $\Omega$, dS is an area element in a boundary $\partial\Omega$ of the region of interest $\Omega$, and n is a normal vector at the boundary $\partial\Omega$. A first term and a second term of Equation (18) are volume integral term and a surface integral term, respectively. On the other hand, a third term of Equation (18) is a divergence-free vector field. Equation (18) is an identity that holds for any three-dimensional vector field.

At step S120, Helmholtz decomposition of the dual field is performed. That is, by substituting the dual field introduced at step S100 into Equation (18), the dual field can be decomposed into a sum of a rotation-free vector field and a divergence-free vector field. A volume integral term of the rotation-free vector field thus decomposed is expressed by using a divergence of a dual field.

For example, in the case of MREPT, because the dual field is Ẽ (quantity that is expressed with a tilde), by substituting this into Equation (18), following Equation (19) is obtained.

$$\tilde{E}(r') = \left( \int_\Omega (\nabla \cdot \tilde{E}) \nabla \frac{1}{4\pi |r'-r|} dv - \int_{\partial\Omega} (n \cdot \tilde{E}) \nabla \frac{1}{4\pi |r'-r|} dS \right) + \int_\Omega (\tilde{E} \times \nabla) \times \nabla \frac{1}{4\pi |r'-r|} dv \quad (19)$$

That is, in the case of MREPT, at step S120A in FIG. 3, Helmholtz decomposition is performed on the dual field Ẽ (quantity that is expressed with a tilde). Thus, the dual field Ẽ (quantity that is expressed with a tilde) can be decomposed into a sum of a rotation-free vector field and a divergence-free vector field as Equation (19). A volume integral term of the rotation-free vector field thus decomposed is expressed by using a divergence of the dual field E (quantity that is expressed with a tilde).

Moreover, in the case of QCM, because the dual field is $\psi$, by substituting this into Equation (18), following Equation (20) is obtained.

$$\psi(r') = \left( \int_\Omega (\nabla \cdot \psi) \nabla \frac{1}{4\pi |r'-r|} dv - \int_{\partial\Omega} (n \cdot \psi) \nabla \frac{1}{4\pi |r'-r|} dS \right) + \int_\Omega (\psi \times \nabla) \times \nabla \frac{1}{4\pi |r'-r|} dv \quad (20)$$

That is, in the case of QCM, at step S120B in FIG. 4, Helmholtz decomposition is performed on the dual field $\psi$. Thus, the dual field $\psi$ can be decomposed into a sum of a rotation-free vector field and a divergence-free vector field as Equation (20). A volume integral term of the rotation-free vector field thus decomposed is expressed by using a divergence of the dual field $\psi$.

Moreover, in the case of MRE, because the dual field is $\sigma_m$, by substituting this into Equation (18), following Equation (21) is obtained.

$$\sigma_m(r') = \left( \int_\Omega (\nabla \cdot \sigma_m) \nabla \frac{1}{4\pi |r'-r|} dv - \int_{\partial\Omega} (n \cdot \sigma_m) \nabla \frac{1}{4\pi |r'-r|} dS \right) + \int_\Omega \left( (\sigma_m^T \times \nabla) \times \nabla \frac{1}{4\pi |r'-r|} \right)^T dv \quad (21)$$

At step S120C in FIG. 5, Helmholtz decomposition is performed on the dual field $\sigma_m$. Thus, the dual field $\sigma_m$ can be decomposed into a sum of a rotation-free vector field and a divergence-free vector field as Equation (21). A volume integral term of the rotation-free vector field thus decomposed is expressed by using a divergence of the dual field $\sigma_m$.

Subsequently, processing at step S130 in FIG. 2 will be explained. The divergence of a dual field is expressed by using the measurement field as described at step S100. Because the volume integral term of a rotation-free vector field obtained by performing Helmholtz decomposition of the dual field can be expressed by using a divergence of the dual field, by substituting an equation indicating that the divergence of the dual field is the measurement field, the volume integral term of the rotation-free vector field can be expressed by using the measurement field. Furthermore, as explained at step S110, because the dual field can be expressed as the second equation using the measurement field and an unknown quantity having spatial dependence, by substituting this second equation into an expression of Helmholtz decomposition, the processing circuit 150 can acquire the first equation, which is a equation between the measurement field and the unknown quantity having spatial dependence by using the calculating function 139.

As described at step S130, the processing circuit 150 can obtain the first equation between the measurement field and the unknown quantity having spatial dependence based on the second equation, which is a equation in which the dual field is expressed by using the measurement field and the unknown quantity having spatial dependence, and on Helmholtz decomposition of the dual field by using the calculating function 139.

Considering an advantage of such a method that the divergence of a dual field is a measurement field, for example, in the example of MREPT, when the left side of Equation (11) is specifically calculated by substituting Equation (12) into Equation (11), $\nabla \cdot (\lambda e \nabla_c H^+) = \nabla \lambda e \cdot \nabla_c H^+ + \lambda e \nabla \cdot (\nabla_c H^+)$ is acquired by a vector analysis formula, although the left side of Equation (11) has a complicated form in which the term including $\nabla \lambda e$, that is, a spatial derivative term of the unknown quantity having spatial dependence and a spatial derivative of the measurement field are combined, the sum of these is the right side of Equation (11), and is a simple expression of a constant multiplication of the measurement field itself. Therefore, regarding the divergence of the dual field as the measurement field, a term of the divergence of the dual field that appears as a result of Helmholtz decomposition can be replaced with the measurement field, and the spatial derivative term of an unknown quantity having spatial dependence can be removed from an integral equation expressing the first expression. That is, the first equation is an integral equation from which the spatial derivative term of the unknown quantity is removed. As a result, a calculation algorithm becomes numerically stable, and an image quality to be acquired becomes stable.

Subsequently, the processing at step S130 will be described specifically about respective application examples. For example, in the case of MREPT, when Equation (11) is substituted into a divergence part of the dual field E (quantity that is expressed with a tilde) in the rotation-free vector field of the first term of the right side of Equation (19), and Equation (12) is substituted into a remaining part of the dual field E (quantity that is expressed with a tilde), following Equation (22) is obtained.

$$\lambda_e \nabla_c H^+ = \tag{22}$$
$$\left( \int_\Omega i\omega\mu_0 H^+ \nabla \frac{1}{4\pi|r'-r|} dv - \int_{\partial\Omega} (n \cdot \lambda_e \nabla_c H^+) \nabla \frac{1}{4\pi|r'-r|} dS \right) +$$
$$\int_\Omega (\lambda_e \nabla_c H^+ \times \nabla) \times \nabla \frac{1}{4\pi|r'-r|} dv$$

That is, at step S130A in FIG. 3, based on Equation (12) that is an equation expressing the dual field E (quantity that is expressed with a tilde) with the measurement field $H^+$ and the unknown quantity $\lambda_e$ having spatial dependence, and Equation (19) that is Helmholtz decomposition of the dual field E (quantity that is expressed with a tilde), Equation (22) that is an equation between the measurement field $H^+$ and the unknown quantity $\lambda_e$ having spatial dependence can be obtained.

Moreover, for example, in the case of QCM, when Equation (14) is substituted to the divergence part of the dual field φ in the rotation-free vector field of the first term of the right side of Equation (20), and Equation (15) is substituted into a remaining part of the dual field ψ, following Equation (23) is obtained.

$$\rho_e \nabla \phi = \left( \int_\Omega 2\omega\mu_0 \nabla \frac{1}{4\pi|r'-r|} dv - \int_{\partial\Omega} (n \cdot \rho_e \nabla \phi) \nabla \frac{1}{4\pi|r'-r|} dS \right) + \tag{23}$$
$$\int_\Omega (\rho_e \nabla \phi \times \nabla) \times \nabla \frac{1}{4\pi|r'-r|} dv$$

That is, at step S130B in FIG. 4, based on Equation (15) that is an equation expressing the dual field ψ with the measurement field φ and the unknown quantity $\rho_e$ having spatial dependence, and Equation (19) that is Helmholtz decomposition of the dual field E (quantity that is expressed with a tilde), Equation (23) that is an equation between the measurement field φ and the unknown quantity $\rho_e$ having spatial dependence can be obtained.

Further, for example, in the case of MRE, when Equation (16) is substituted to the divergence part of the dual field σm in the rotational-free vector field of the first term of the right side of Equation (21) and Equation (17) is substituted into the remaining part of the dual field σm, following Equation (24) is obtained.

$$\lambda_m \nabla \cdot uI + \mu_m(\nabla u + (\nabla u)^T) = -\int_\Omega \omega_1^2 \rho_m u \nabla \frac{1}{4\pi|r'-r|} dv + \tag{24}$$
$$\int_{\partial\Omega} (n \cdot (\lambda_m \nabla \cdot uI + \mu_m(\nabla u + (\nabla u)^T))) \nabla \frac{1}{4\pi|r'-r|} dS +$$
$$\int_\Omega \left( ((\lambda_m \nabla \cdot uI + \mu_m(\nabla u + (\nabla u)^T))^T \times \nabla) \times \nabla \frac{1}{4\pi|r'-r|} \right)^T dv$$

That is, at step S130C in FIG. 5, based on Equation (17) that is an equation expressing the dual field $\sigma_m$ with the displacement u and the elastic constants $\lambda_m$, $\mu_m$ which are an unknown quantity having spatial dependence, and Equation (21) that is Helmholtz decomposition of the dual field $\sigma_m$, Equation (24) that is an equation between the displacement u and the elastic constants λm, μm, which are the unknown quantity having spatial dependence is derived.

Subsequently, step S140 in FIG. 2 will be explained again. At step S140, the measurement field corresponding to a spatial distribution of a predetermined physical quantity in the subject of measurement is acquired, and an unknown quantity in the subject of measurement is calculated based on the acquired measurement field and the equation acquired at step S130. Specifically, at step S140, first, the processing circuit 150 acquires a measurement field corresponding to a spatial distribution of a predetermined physical quantity in the subject of measurement by using the acquiring function 138.

For example, in the case of MREPT, the processing circuit 150 acquires, by the acquiring function 138, for example, by the receiver circuit 110, the RF magnetic field $H^+$ as the measurement field by the method described above.

In the case of QCM, the processing circuit 150 acquires, by the acquiring function 138, for example, by the receiver circuit 110, a phase of the RF magnetic field $H^+$ as the measurement field φ.

In the case of MRE, the subject P is placed in a static magnetic field of an MRI apparatus, and a vibration generating device not illustrated applies sinusoidal lateral vibration, for example, externally to the subject. The sequence control circuit 120 performs pulse sequence of a gradient magnetic field motion probing gradients (MPG) phase shift method in which positive and negative polarities are alternately repeated, for example, in synchronization with external vibrations. The processing circuit 150 acquires a signal relating to the pulse sequence by the acquiring function 138. The processing circuit 150 acquires information relating to the displacement u based on the acquired signal.

Subsequently, the processing circuit 150 estimates an unknown quantity having spatial dependence based on the acquired measurement field, and on the first equation between the measurement field and the unknown quantity having spatial dependence acquired at step S130 described later.

For example, in the case of MREPT, as indicated at step S140A in FIG. 3, the processing circuit 150 calculates the impedance $\lambda_e$ or the conductivity $\sigma_e$/permittivity $\varepsilon$ that are an unknown quantity spatially varying in the subject of measurement based on the acquired measurement field H⁺ and Equation (22) that is the equation acquired at step S130A by using the calculating function 139.

For example, in the case of QCM, as indicated at step S140B in FIG. 4, the processing circuit 150 calculates the conductivity $\sigma_e$/resistivity $\rho e$ that is an unknown quantity spatially varying in the subject of measurement based on the acquired measurement field $\phi$ and Equation (23) that is the equation acquired at step S130B, by using the calculating function 139.

For example, in the case of MRE, as indicated at step S140C in FIG. 5, the processing circuit 150 calculates the elastic constants $\lambda_m$, $\mu_m$ and the like that are an unknown quantity spatially varying in the subject of measurement based on the displacement u, which is the acquired measurement field, and Equation (24) that is the equation acquired at step S130C, by using the calculating function 139.

Subsequently, advantage of generating an image by using Equation (22) to Equation (24) that are equations in which a dual field is expressed by using a measurement field and an unknown quantity having spatial dependence will be explained. Characteristics of these equations include that any of them is a linear integral equation relating to an unknown quantity. Therefore, a solution can be acquired directly without using an iterative method. On the other hand, when the integral equation is not a linear equation relating to an unknown quantity, calculation using an interactive method is necessary, and it can run into a local optimal solution depending on an initial solution. However, in the method according to the embodiment, a solution can be acquired directly without using an iterative method.

Moreover, these equations do not include a second order spatial derivative term relating to a measurement field. Therefore, it is to be an imaging method robust against noises. For example, in the case of MREPT, even in the case when the conductivity discontinuously changes compared to a normal tissue, such as a case of a localized solid cancer, the measurement accuracy of the conductivity or the permittivity is less prone to be reduced, and these tissues or the like can be visualized at preferable contrast, or quantitative evaluation can be performed.

Furthermore, conventionally, by the method using integral representation, there has been a case in which an integral representation of an electromagnetic field in the entire region is used. In this case, for example, it is necessary to include an MRI coil and the like in the region for which integration is performed as a source of the electromagnetic field and, therefore, to remove an influence of the MRI coil, it has also been necessary to measure or calculate an electromagnetic field at no load. On the other hand, in the method according to the embodiment, Helmholtz decomposition can be limited to a bounded region of interest, and measurement or calculation of an electromagnetic field at no load becomes unnecessary.

At this step of calculating an unknown quantity by the processing circuit 150 by using the calculating function 139 by solving Equation (22) to Equation (24), the region of interest $\Omega$ in Equation (22) to Equation (24), which are the first equation, may be identified by imaging a structural image of a subject, and step S140 may be performed based on the identified region of interest $\Omega$. Thus, the accuracy of estimation of an unknown quantity can be further improved.

In FIG. 8, one example of a procedure of the processing at step S140 in the embodiment as described above is illustrated. That is, steps S141 to S143 are one example of step S140 in FIG. 2. In the following, an example in which magnetic resonance imaging of, for example, a region of a brain is performed will be explained.

First, the sequence control circuit 120 performs the pulse sequence to perform imaging to generate a structural image of the subject of measurement. For example, when the subject of measurement is a brain, the sequence control circuit 120 performs a pulse sequence to perform imaging of the brain.

At step S141, the processing circuit 150 acquires, from the sequence control circuit 120, a magnetic resonance signal collected based on the pulse sequence performed by the sequence control circuit 120, and acquires a structural image of the subject of measurement based on the acquired magnetic resonance signal. For example, when the subject of measurement is a brain, the processing circuit 150 acquires a structural image of a region of a brain by magnetic resonance imaging, based on the magnetic resonance signal by the pulse sequence performed by the sequence control circuit 120.

Subsequently, at step S142, the processing circuit 150 performs segmentation processing with respect to the subject of measurement included in the structural image, and thereby identifies the measurement subject region $\Omega$ (region of interest $\Omega$) in which a measurement field is acquired from the subject of measurement by the acquiring function 138, by using the identifying function 137. As one example, when the subject of measurement is a brain, the processing circuit 150 identifies a region of a substantial part of the brain as the measurement subject region $\Omega$ (region of interest $\Omega$) by segmentation processing based on the structural image acquired at step S141, by the identifying function.

Subsequently, at step S143, the processing circuit 150 acquires a measurement field in the measurement subject region $\Omega$ (region of interest $\Omega$) acquired by the acquiring function 138, and calculates an unknown quantity based on the measurement field in the measurement subject region $\Omega$ (region of interest $\Omega$) by the calculating function 139. As one example, the processing circuit 150 acquires the measurement field in the region of the substantial part of the brain by the acquiring function 138, and calculates the unknown quantity by solving Equation (22) to Equation (24), which are the first equation, with respect to subject region $\Omega$ by the calculating function 139. Thus, the accuracy of estimation of an unknown quantity can be improved.

Moreover, as another advantage of generating an image by using Equation (22) to Equation (24), the fact that the regularization is easily incorporated because these are linear integral equations can be mentioned.

In the case of MREPT, at the point at which the dual field E (quantity that is expressed with a tilde) becomes zero, both the left side and the right side of Equation (22) are also zero, and $\lambda_e$ is not determined. In fact, explaining a case in which a numerical phantom as illustrated in (a) in FIG. 9 is used, as in (b) in FIG. 9, at the point at which a field E (quantity that is expressed with a tilde) of the left side of Equation (22), an artifact occurs in an estimation image of the conductivity in a corresponding region 10 as illustrated in (c) in FIG. 9. Particularly, when a noise is added to observation data H⁺, this influence becomes significant as in (d) in FIG. 9.

In such a case, instead of directly solving the integral equation of Equation (22), for example, as in following Equation (25), a function in which a regularization term R(x) (x is a vector quantity) is added to a first term, which is a square error of the left side and the right side of the integral equation of Equation (22), is used as an evaluation function, and by minimizing the evaluation function, the processing circuit 150 can calculate an unknown quantity by the calculating function 139.

$$\|Ax-b\|^2 + \alpha^2 R(x) \to \min \quad (25)$$

x is an unknown vector in which $\lambda_e$ that is an unknown quantity is aligned as many as the number of pixels, A and b are a coefficient matrix and a right side vector determined from Equation (22). The regularization term R(x) is a term added so as to make the unknown quantity λe spatially smooth, and this reduces the artifact, and the image quality is improved.

In other words, the first equation, which is the equation between the measurement field and the unknown quantity expressed by Equation (22) to Equation (24), can have a singular point around which the numerical calculation becomes unstable, such as near a zero point of the dual field. On the other hand, by performing the regularization, that is, based on the evaluation function constituted of a term acquired from the first equation and a regularization term, the processing circuit 150 can calculate the unknown quantity by the calculating function 139. Thus, the numerical stability around a singular point that is present in the first equation improves, and the image quality improves.

Examples of the calculation result are shown in (e), (f) in FIG. 9. A result when following Equation (26) in which R(x) is L2 norm of x is used is in FIG. 9 (e), and a result when following Equation (27) in which R(x) is a total variation of x is in FIG. 9 (f), and in either cases, reduction of artifact is observed.

$$\|Ax-b\|^2 + \alpha^2 \|x\|^2 \to \min \quad (26)$$

$$\|Ax-b\|^2 + \alpha^2 (\|D_x x\|_1 \|D_y x\|_1) \to \min \quad (27)$$

Note that how the regularization term is given is not limited to these two examples.

The processing in the case of MREPT has been explained, but in the case of QCM and MRE instead of Equation (25) derived based on Equation (22), by deriving Equation (25) based respectively on Equation (23) and Equation (24), similar regularization processing can be performed.

That is, in the case of QCM, in Equation (25), x in the regularization term R(x) is an unknown vector in which $\rho_e$, which is an unknown quantity, is aligned as many as the number of pixels, and A and b are a matrix determined from Equation (23) and a right side vector. The processing circuit 150 calculates the unknown quantity $\rho_e$ based on Equation (25) thus derived, by the calculating function 139.

Moreover, in the case of MRE, in Equation (25), x in the regularization term R(x) is an unknown vector in which the unknown quantities $\lambda_m$ and $\mu_m$ are aligned as many as the number of pixels, and A and b are a matrix determined from Equation (24) and a right side vector. The processing circuit 150 calculates the unknown quantities $\lambda_m$ and $\mu_m$ based on Equation (25) thus derived by the calculating function 139.

According to at least one of embodiments explained above, the image quality can be improved.

Some embodiments have been explained, but these embodiments are only an example, and are not intended to limit the scope of the invention.

For example, it has been described that in Equation (11), the divergence of the field E (quantity that is expressed with a tilde) of the left side is a multiplication of the measurement field and a constant, and that a field in which its divergence is expressed with the measurement field $H^+$ is the dual field of the measurement field $H^+$. However, definition of a dual field is not limited thereto. For example, E tilde that is a quantity satisfying both Equation (11) derived from Faraday's law and Equation (12) derived from Ampere's law may be referred to as dual field of $H^+$.

Moreover, similarly, it has been described that in the case of QCM, for example, in Equation (14), the divergence of the field ϕ of the left side is a constant, and that a field in which its divergence is expressed by zero power of the measurement field ϕ is the dual field of the measurement field ϕ. However, definition of the dual field is not limited thereto. For example, ψ that is a quantity satisfying both Equation (14) derived from Faraday's law and Equation (15) derived from Ampere's law may be referred to as dual field of the measurement field ϕ.

Furthermore, similarly, it has been described that in the case of MRE, for example, in Equation (16), the divergence of the field $\sigma_e$ of the left side is a constant multiplication of the measurement field, and that a field in which its divergence is expressed by the measurement field u is a dual field of the measurement field u. However, definition of the dual field is not limited thereto. For example, $\sigma_m$ that is a quantity satisfying both Equation (16) derived from an equation of motion and Equation (17) derived from Hooke's law may be referred to as dual field of the measurement field u.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An information processing apparatus comprising
a processing circuit configured to acquire a measurement field corresponding to a spatial distribution of a predetermined physical quantity in a subject of measurement, and calculate an unknown quantity in the subject of measurement based on a first equation between the measurement field and the unknown quantity having spatial dependence, and on the acquired measurement field, wherein
the first equation is one that is acquired based on a second equation expressing a dual field divergence of which is capable of being expressed using the measurement field by using the measurement field and the unknown quantity, and on the Helmholtz decomposition of the dual field.

2. The information processing apparatus according to claim 1, wherein the first equation is an integral equation from which a spatial derivative term of the unknown quantity is removed.

3. The information processing apparatus according to claim 1, wherein
the measurement field is an RF (high frequency) magnetic field, and the unknown quantity includes at least one of a conductivity and a permittivity.

4. The information processing apparatus according to claim 3, wherein
the measurement field is an amplitude and a phase of the RF magnetic field.

5. The information processing apparatus according to claim 4, wherein
   magnetic resonance electrical property tomography (MREPT) is performed based on the unknown quantity calculated by the processing circuit.

6. The information processing apparatus according to claim 3, wherein
   the measurement field is a phase of the RF magnetic field, and
   Quantitative conductivity mapping (QCM) is performed based on the unknown quantity calculated by the processing circuit.

7. The information processing apparatus according to claim 1, wherein
   the measurement field is a displacement, and the unknown quantity includes at least one of a coefficient of elasticity and a coefficient of viscosity.

8. The information processing apparatus according to claim 1, wherein
   the measurement field is a displacement, and the dual field is a stress tensor.

9. The information processing apparatus according to claim 1, wherein
   magnetic resonance elastography (MRE) is performed based on the unknown quantity calculated by the processing circuit.

10. The information processing apparatus according to claim 1, wherein
    the first equation is one that is derived from Ampere's law and Faraday's law.

11. The information processing apparatus according to claim 1, wherein
    the first equation is one that is derived from an equation of motion of an elastic body and Hooke's law.

12. The information processing apparatus according to claim 1, wherein
    the processing circuit is configured to acquire a structural image of a subject of measurement, identify a measurement subject region in which the measurement field is acquired from the subject of measurement by performing segmentation processing with respect to the subject of measurement included in the structural image, and calculate the unknown quantity based on the measurement field in the measurement subject region.

13. The information processing apparatus according to claim 12, wherein
    the subject of measurement is a brain,
    the processing circuit is configured to acquire the structural image of a region of the brain by magnetic resonance imaging, identify a region of a substantial part of the brain as the measurement subject region based on the structural image by the segmentation processing, and calculate the unknown quantity based on the measurement field in the region of the substantial part.

14. The information processing apparatus according to claim 1, wherein
    the processing circuit is configured to calculate the unknown quantity based on an evaluation function including a term acquired from the first equation and a regularization term.

15. An information processing method comprising:
    acquiring a measurement field corresponding to a spatial distribution of a predetermined physical quantity in a subject of measurement; and
    calculating an unknown quantity in the subject of measurement based on a first equation between the measurement field and the unknown quantity having spatial dependence, and on the acquired measurement field, wherein
    the first equation is one that is acquired based on a second equation expressing a dual field divergence of which is capable of being expressed using the measurement field, by using the measurement field and the unknown quantity, and on the Helmholtz decomposition of the dual field.

* * * * *